(12) United States Patent
Yoon et al.

(10) Patent No.: US 10,512,494 B2
(45) Date of Patent: Dec. 24, 2019

(54) PEDICLE SCREW WITH QUADRUPLE SCREW THREAD

(71) Applicant: MANTIZ LOGTECH CO., LTD., Daegu (KR)

(72) Inventors: Hong Won Yoon, Busan (KR); Kwang Hoon Lee, Pyeongtaek-si (KR)

(73) Assignee: MANTIZ LOGTECH CO., LTD., Daegu (KR)

( * ) Notice: Subject to any disclaimer, the term of this patent is extended or adjusted under 35 U.S.C. 154(b) by 25 days.

(21) Appl. No.: 15/868,882

(22) Filed: Jan. 11, 2018

(65) Prior Publication Data

US 2018/0206896 A1 Jul. 26, 2018

(30) Foreign Application Priority Data

Jan. 23, 2017 (KR) .................. 10-2017-0010185

(51) Int. Cl.
*A61B 17/86* (2006.01)
*A61B 17/70* (2006.01)

(52) U.S. Cl.
CPC ........ *A61B 17/863* (2013.01); *A61B 17/7001* (2013.01)

(58) Field of Classification Search
CPC ... A61B 17/863; A61B 17/84; A61B 17/8625; A61B 17/86
See application file for complete search history.

(56) References Cited

U.S. PATENT DOCUMENTS

| 6,129,730 | A | * | 10/2000 | Bono | A61B 17/8047 |
| | | | | | 606/271 |
| 9,247,976 | B2 | | 2/2016 | Denis et al. | |
| 2008/0194348 | A1 | * | 8/2008 | Ferrell | B21H 3/02 |
| | | | | | 470/72 |
| 2013/0053901 | A1 | | 2/2013 | Cormier et al. | |
| 2014/0012334 | A1 | * | 1/2014 | Armstrong | A61B 17/863 |
| | | | | | 606/309 |

\* cited by examiner

*Primary Examiner* — Lynnsy M Summitt
*Assistant Examiner* — Tara Rose E Carter
(74) *Attorney, Agent, or Firm* — Maschoff Brennan (57) ABSTRACT

A pedicle screw has quadruple screw threads capable of moving forward a long distance in a bone upon rotation. For a screw to be embedded in a dense cortical bone of a vertebra, the threads include relief screw threads, to strongly couple with bone tissue in the cortical bone. For a screw to be embedded in a cancellous bone of the vertebra, two lines of threads (odd or even) include relief screw threads while the other two lines of threads include intaglio screw threads, thereby more strongly coupling with relatively soft cancellous bone tissue. The threads are provided in the whole pedicle screw, to move forward at 4-fold higher speed than a single screw thread, and intaglio screw threads are formed at a position to which the cancellous bone is fixed, so that cancellous bone tissues penetrate between the intaglio threads, thereby strongly coupling to the cortical and cancellous bones.

8 Claims, 7 Drawing Sheets

PEDICLE SCREW WITH QUADRUPLE SCREW THREAD

TECHNICAL FIELD

The present invention relates to a pedicle screw with quadruple screw threads and, more particularly, to a pedicle screw with quadruple screw threads, capable of being strongly coupled to a vertebra by applying a structure suitable for a cortical bone and a cancellous bone.

BACKGROUND ART

The spinal column, better known as the backbone or spine, is a highly complex system comprising connective tissues for bones to offer a support part for the human body and protect sensitive spinal cord and nerve roots. The spine includes a series of vertebrae stacked one on top of the other, and a pedicle of each vertebra includes an inner part composed of relatively soft cancellous bones and an outer part composed of stronger cortical bones.

For treatment of diseases related to the spine, an indirect treatment method using physical therapy and a direct method of correcting or fixing the spine by mounting an alternative fixation device to an injured pedicle are typically conducted. Physical therapy is often used for slight spinal disorders, however, in case of serious diseases of cervical vertebra, thoracic vertebra, lumbar vertebra, sacrum, intervertebral disk or the like, which form the spine, treatment using a spinal fixation device is normally performed.

As one of the direct treatment methods described above, spinal fixation using a spinal fixation device refers to a technique to fix the spine by using an orthopedic rod, which approximately extends in parallel to the spine and is typically called a 'spine rod,' and may be accomplished by exposing the back portion of the spine and inserting a spine fixation screw into the pedicle of a desired vertebra.

Generally, two spine fixation screws are mounted on each vertebra and function as a fixation point for the spine rod. Therefore, an arrangement of the spine rods allows the spine to be fixed in a more advantageous shape. Such a spine fixation screw consists of a screw rod to be inserted and fixed in the pedicle and a screw head integrally coupled with the screw rod.

A conventional and traditional spine fixation screw does not have any structural difference between a part of a screw thread in the screw rod to be inserted and fixed in the pedicle, which is embedded in a cancellous bone, and another part thereof, which is embedded in a cortical bone, thus causing a problem that the spin fixation screw could not be strongly coupled with bone tissues.

In other words, since the cancellous bone is a soft bone tissue region while the cortical bone is a region composed of relatively rigid and compact outer bone, it is important that the spin fixation screw has a structure including a screw rod and a screw thread exactly matching with each region. If not, a coupling of a screw member to the region may be loosened by external force, which in turn does not offer sufficient coupling force and resistance required to fix the spine. As a result, there is a problem of difficulties in fixing an injured spine.

In order to solve the above problem, a variety of conventional methods have been invented, including, for example, U.S. Pat. No. 9,247,976 B2 (entitled "Multiple-thread bone screw and method thereof") and US Patent Laid-Open Publication No. US 2013/0053901 A1 (entitled "Bone anchor").

Figure 1:
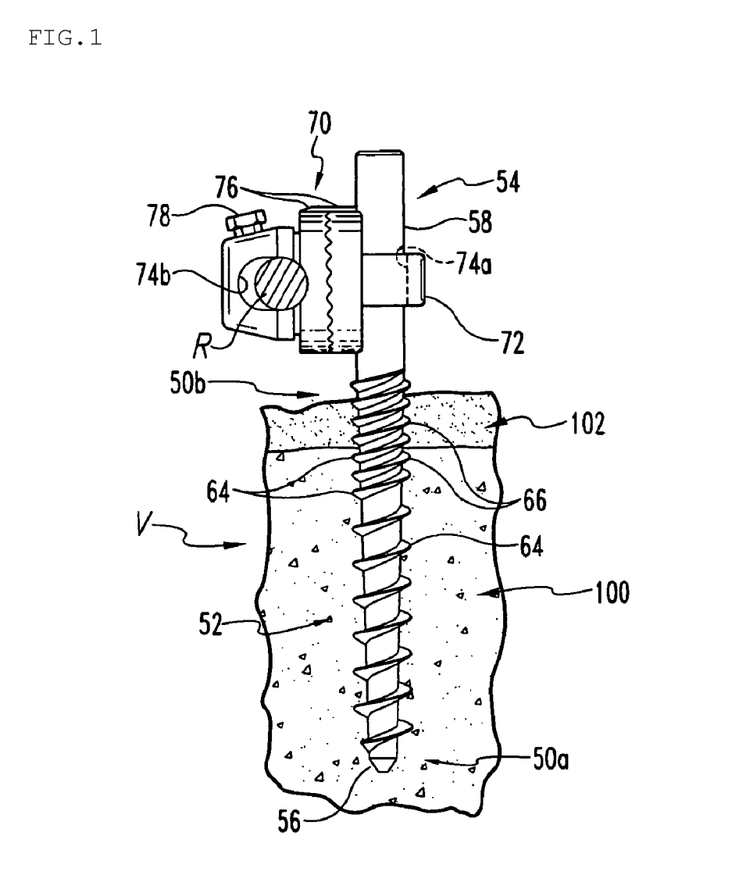
FIG. 1 is a view illustrating a bone screw according to a conventional design, which is coupled to a bone.
Figure 2:
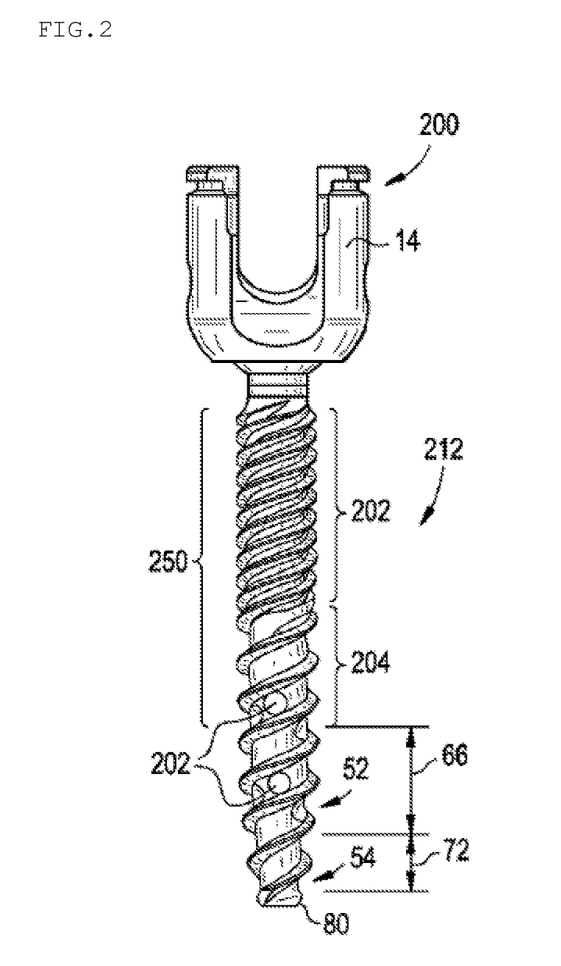
FIG. 2 is a view illustrating a bone screw according to another conventional design.

U.S. Pat. No. 9,247,976 B2 describes that a screw body fixed to a cancellous bone 100 forms a single-strand screw pattern while another screw body fixed to a cortical bone 102 forms a double-strand screw pattern (see FIG. 1). US Patent Laid-Open Publication No. 2013/0053901 A1 describes that a distal screw thread connecting part 204, second screw thread connecting part 52 and third screw thread connecting part 54 are all double screw thread types while a proximal screw thread connecting part 202 is a quadruple screw thread type (see FIG. 2).

As such, according to the disclosures of U.S. Pat. No. 9,247,976 B2 and US Patent Laid-Open Publication No. 2013/0053901 A1, a screw thread of the screw body fixed to the cortical bone is more densely formed, compared to a screw thread of the screw body fixed to the cancellous bone.

PRIOR ART DOCUMENT

Patent Document

U.S. Pat. No. 9,247,976 B2
US Patent Laid-Open Publication No. 2013/0053901 A1

DISCLOSURE

Technical Problem

The present invention has been proposed to more efficiently improve the prior art as described above, and one object of the present invention is to provide a pedicle screw with quadruple screw threads, which includes the quadruple screw threads capable of moving forward a long distance in a bone upon rotation, wherein: the quadruple screw threads corresponding to a part embedded in the cortical bone of a vertebra densely comprise relief screw threads throughout the same, so as to be strongly coupled with bone tissues in the cortical bone. On the other hand, among the above quadruple screw threads, two lines of screw threads (odd or even lines) corresponding to a part embedded in the cancellous bone of the vertebra comprise relief screw threads while the other two lines of screw threads (even or odd lines) comprise counter-relief ('intaglio') screw threads, thereby being more strongly coupled with relatively soft cancellous bone tissue.

In other words, there is a wide space between two lines of relief screw threads coupled to the cancellous bone and intaglio screw threads are formed by cutting a threaded root between the relief screw threads with a predetermined width and a predetermined depth, and therefore, the cancellous bone tissues may penetrate between the intaglio screw threads. Consequently, it is possible to provide a pedicle screw with quadruple screw threads capable of being more strongly coupled with the cancellous bone tissues, as compared to the prior art.

Technical Solution

In order to accomplish the above object, in accordance with one aspect of the present invention, provided is a pedicle screw with quadruple screw threads, including: a screw body extending from a proximal end to a distal end so as to be fixed to a vertebra; a joint head provided at an end of the screw body; a first screw part, which is formed from the proximal end of the screw body and has a quadruple screw thread pattern for fixing the same to a cortical bond; and a second screw part, which is formed following the first screw part toward the distal end and has another quadruple screw thread pattern for fixing the same to a cancellous bone, wherein the quadruple screw pattern formed in the first screw part is a relief pattern throughout the same, while two lines of screw threads (odd or even lines) in the second screw part are formed in relief but an other two lines of screw threads (even or odd lines) in the same are formed in intaglio.

In this case, each of the screw threads forming the quadruple screw thread pattern of the first screw part is formed at a position 90° from a circumference of the screw body.

Further, the second screw part occupies ½ to ⅔ of the screw body.

Furthermore, a minor diameter of the first screw part is larger than that of the second screw part and is formed with a fixed size throughout the same. On the other hand, a minor diameter of the second screw part entirely has a fixed size except for the distal end.

Further, the intaglio screw thread in the second screw part is formed by cutting the center portion of a threaded root between the relief screw threads with a predetermined width and a predetermined depth.

Further, the predetermined width of the intaglio screw thread substantially corresponds to a bottom width of the relief screw thread.

Further, the intaglio screw thread in the second screw part is formed by cutting a corresponding portion, at which a height of the relief screw thread is finally eliminated after being gradually decreased from an end point of the relief screw thread in the first screw part along a circumference of the screw body, with a predetermined depth.

In particular, the intaglio screw thread in the second screw part is formed by cutting a corresponding portion, at which the relief screw thread is not formed, to achieve a width corresponding to the bottom width of the relief screw thread as well as the predetermined depth.

Advantageous Effects

According to the present invention with the technical configurations as described above, the following effects may be accomplished:

Firstly, the present invention forms a screw body with quadruple screw threads, which can move forward in a bone at 4-fold higher speed than a single screw thread, so as to effectively reduce a time required to fix the pedicle screw by medical staff.

The second screw part of the screw body coupled to the cancellous bone in the vertebra includes two lines (odd or even lines) consisting of relief screw threads and the other two lines (even or odd lines) consisting of intaglio screw threads so that soft cancellous bone tissue is fitted in the intaglio screw threads formed in a wide space between the relief screw threads, thus enabling the pedicle screw to more strongly couple with the cancellous bone tissues. As a result, the inventive pedicle screw can be strongly coupled to not only the cortical bone but also the cancellous bone, and therefore, it is possible to prevent the pedicle screw from loosening or becoming wobbly due to use of the same for a long time.

The intaglio screw threads in the odd or even lines may be formed by cutting a corresponding portion, at which a height of the relief screw threads in the odd or even lines, among the quadruple relief screw threads in the first screw part starting to be formed at the proximal end, is finally eliminated after being gradually decreased from an end point of the relief screw thread in the first screw part along the circumference of the screw body, with a predetermined depth. Therefore, a complicated cutting process is not required and production costs may be reduced.

BEST MODE

Advantages and characteristics of the present invention and a method for accomplishing the same will be more apparent from the following examples with reference to the accompanying drawings.

However, the present invention is not particularly limited to the following examples but may be embodied in different variations.

In this specification, the present examples are provided to complete the description of the present invention and clearly explain the scope of the present invention to a person having ordinary skill in the art, to which the present invention pertains.

Further, the scope of present invention is defined only by the appended claims.

Accordingly, components, motions and techniques well-known in the art in some examples would not be described in detail to avoid ambiguous interpretation of the present invention.

Further, the same symbols refer to the same components in this specification, and terms used (mentioned) in this specification are provided for purpose of describing particular examples only, and are not intended to limit the present invention.

Unless otherwise specified, terms in a singular form used in this specification include a concept of plural, and any component or motion mentioned with 'include' (or 'have') does not exclude the presence or addition of one or more other component(s) or motion(s).

Unless otherwise defined, all terms (including scientific and technological terms) used in this specification may have meanings commonly understood by a person having ordinary skill in the art to which the present invention pertains.

Further, terms defined in a commonly-used dictionary should not be interpreted as being ideally or excessively formal unless specifically so defined herein.

Hereinafter, with reference to the accompanying drawings, preferred embodiments of the present invention will be more concretely described and illustrated.

Referring to FIGS. 3 to 7, the present invention relates to a pedicle screw inserted into a vertebra. Among conventional methods for surgical treatment of scoliosis, pedicle screw insertion is a process of inserting a screw into a bent vertebra to correct the same, more particularly, a method of inserting a pedicle screw into a bent vertebra and using a rod to connect several pedicle screws together, in order to aid in restoration of the spine to a normal state thereof. The pedicle screw of the present invention is applicable to such surgical treatment of scoliosis as described above.

Figure 3:
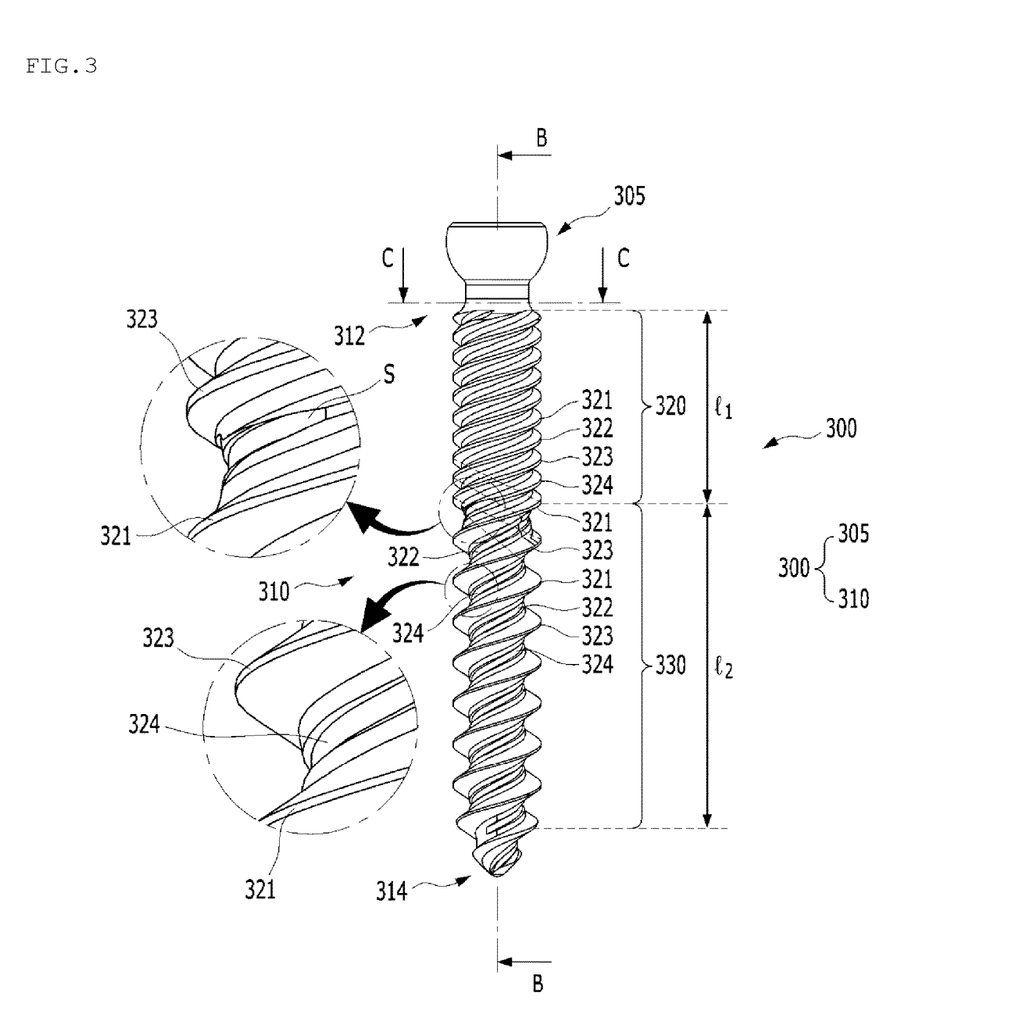
FIG. 3 is a front view illustrating a pedicle screw with quadruple screw threads according to one embodiment of the present invention.
Figure 4:
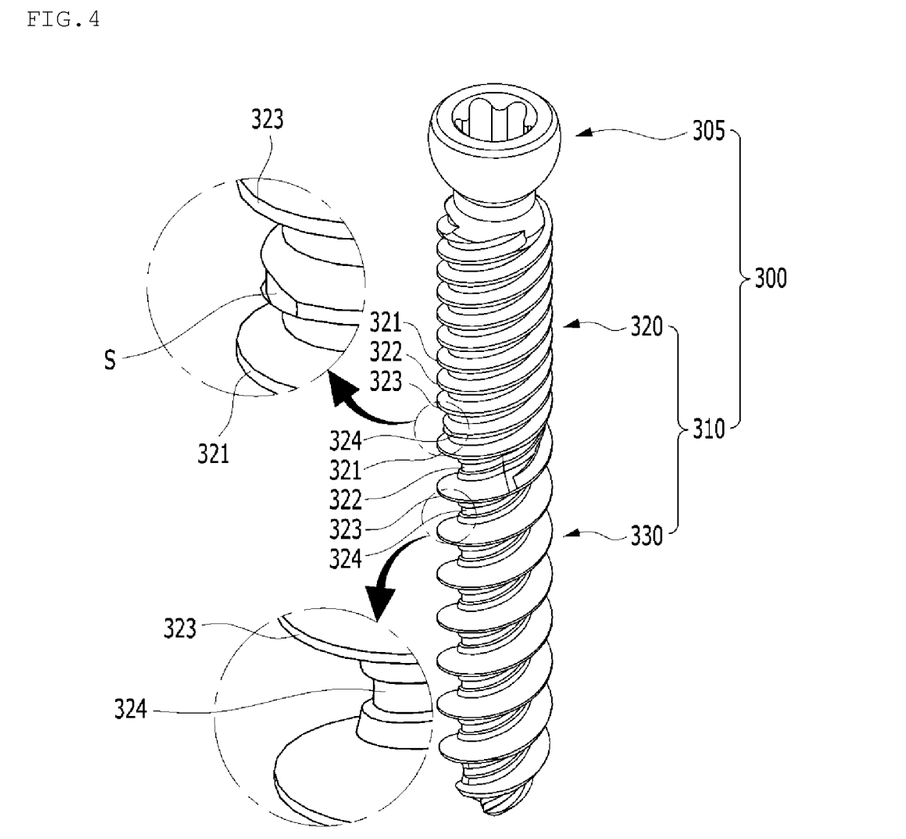
FIG. 4 is a perspective view of the pedicle screw with quadruple screw threads according to the embodiment of the present invention.
Figure 5:
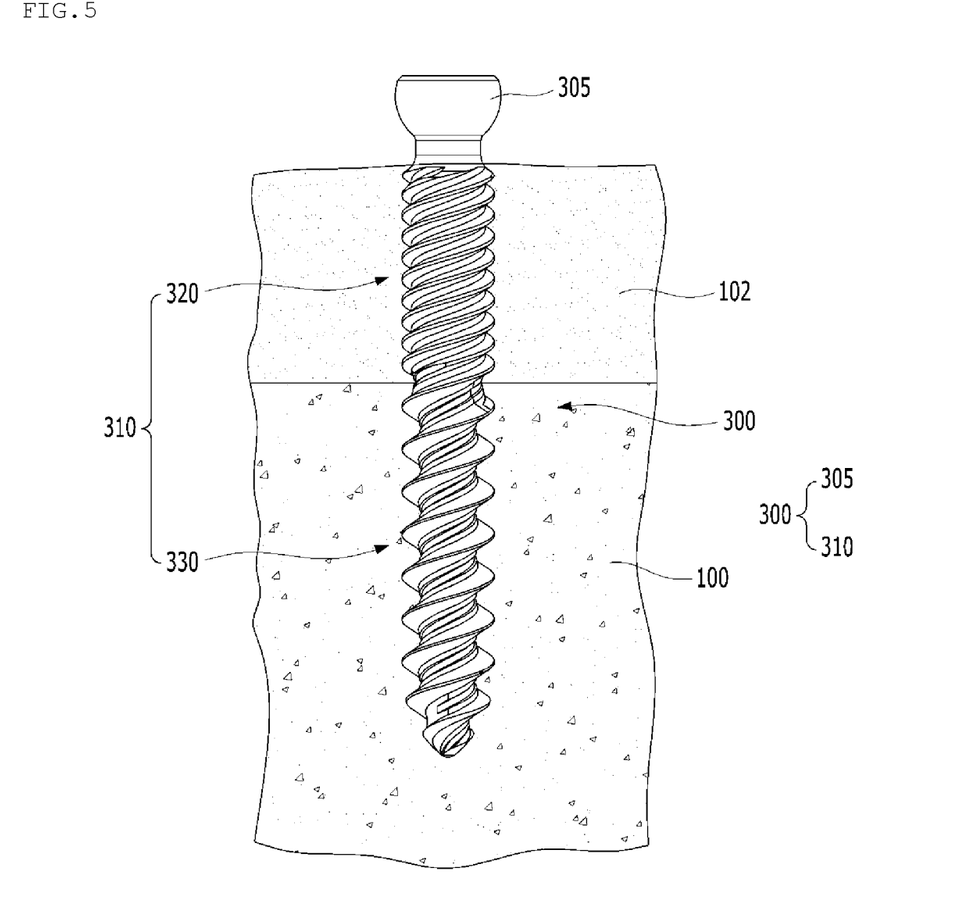
FIG. 5 is a view illustrating the pedicle screw with quadruple screw threads according to the embodiment of the present invention, which is inserted and fixed to a pedicle.

A pedicle screw 300 having quadruple screw threads of the present invention may include: a screw body 310; a joint head 305; a first screw part 320; and a second screw part 330. A head part having an open top (not shown) is coupled to the joint head 305. A rod (not shown) is disposed on top of the joint head 305 seated and fixed on the head part (not shown), which in turn, is coupled to the head part (not shown), such that a vertebra and adjacent vertebrae have a constant gap therebetween.

The pedicle screw 300 may be formed of titanium, stainless steel, a metal alloy or other bio-compatible materials, which are suitable for transplant in a body and adhesion to bone.

The screw body 310 is formed to extend from a proximal end 312 to a distal end 314 and is fixed to the vertebra.

The joint head 305 is provided at an end of the screw body 310. The head part (not shown) as described above is coupled to the joint head 305. The joint head 305 is provided at an end of the first screw part 320.

The first screw part 320 is formed from the proximal end 312 of the screw body 310 and has a quadruple screw thread pattern for fixing the same to a cortical bone 102.

The second screw part 330 is formed following the first screw part 320 of the screw body 310 toward the distal end 314 and has another quadruple screw thread pattern for fixing the same to a cancellous bone 100. Quadruple screw threads in the first screw part 320 and alternative quadruple screw threads in the second screw part 330 are interconnected.

All of the quadruple screw threads 321, 322, 323 and 324 in the first screw part 320 are formed in relief, however, two lines of screw threads (odd or even lines) in the second screw part 330 are formed in relief while the other two lines of screw threads (even or odd lines) are formed in intaglio. The relief and intaglio screw threads in the second screw part 330 are substantially the ones extending from the quadruple screw threads 321, 322, 323 and 324 in the first screw part 320. However, two lines of screw threads among the quadruple screw threads in the first screw part 320 are changed into the intaglio screw threads in the second screw part 330.

Referring to the portion indicated by dotted lines, it can be seen that the relief screw threads 321 and 323 in the first screw part 320 also become the relief screw threads 321 and 323 in the second screw part 330, however, the other relief screw threads 322 and 324 in the first screw part 320 are changed into the intaglio screw threads 322 and 324 in the second screw part 330 (see FIG. 3).

Referring to FIGS. 3 and 4, if the odd lines 321 and 323 of screw threads in the second screw part 330 are formed in relief, the even lines 322 and 324 of screw threads are intaglio. That is, odd and even lines of screw threads are formed in relief and intaglio by turns.

The relief screw threads refer to external screw threads protruding from the first screw part 320 and the second screw part 330, while the intaglio screw threads refer to screw threads concavely cut (or engraved) by additional work in a space between the relief screw threads in the second screw part 330. Such additional work may comprise CNC machining. The intaglio screw threads will be more concretely described below.

Figure 7:
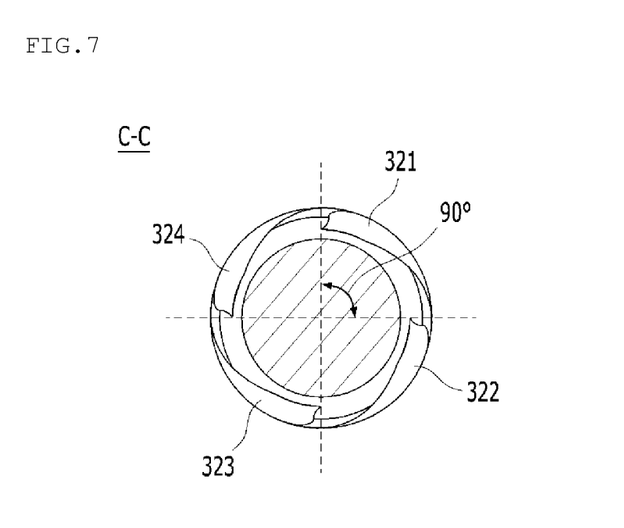
FIG. 7 is a cross-sectional view in direction C-C shown in FIG. 3.

Referring to FIG. 7, each of the screw threads forming the quadruple screw thread pattern in the first screw part 320 is formed at a position 90° from a circumference of the screw body 310. The quadruple relief screw threads 321, 322, 323 and 324 in the first screw part 320 start to form at a position 90° from the central axis of the screw body 310, respectively.

Referring to FIG. 3, the second screw part 330 occupies ½ to ⅔ of the screw body 310. An outer skin portion of the vertebra consists of a cortical bone 102, which comprises compact and rigid tissue and has a relatively small thickness, as compared to a cancellous bone 100 formed of soft and tender tissue. Therefore, it is preferable that a length $l_1$ of the first screw part 320 embedded in the cortical bone 120 comprise about 40% of the screw body 310 while a length $l_2$ of the second screw part 330 comprises about 60% of the same.

Figure 6:
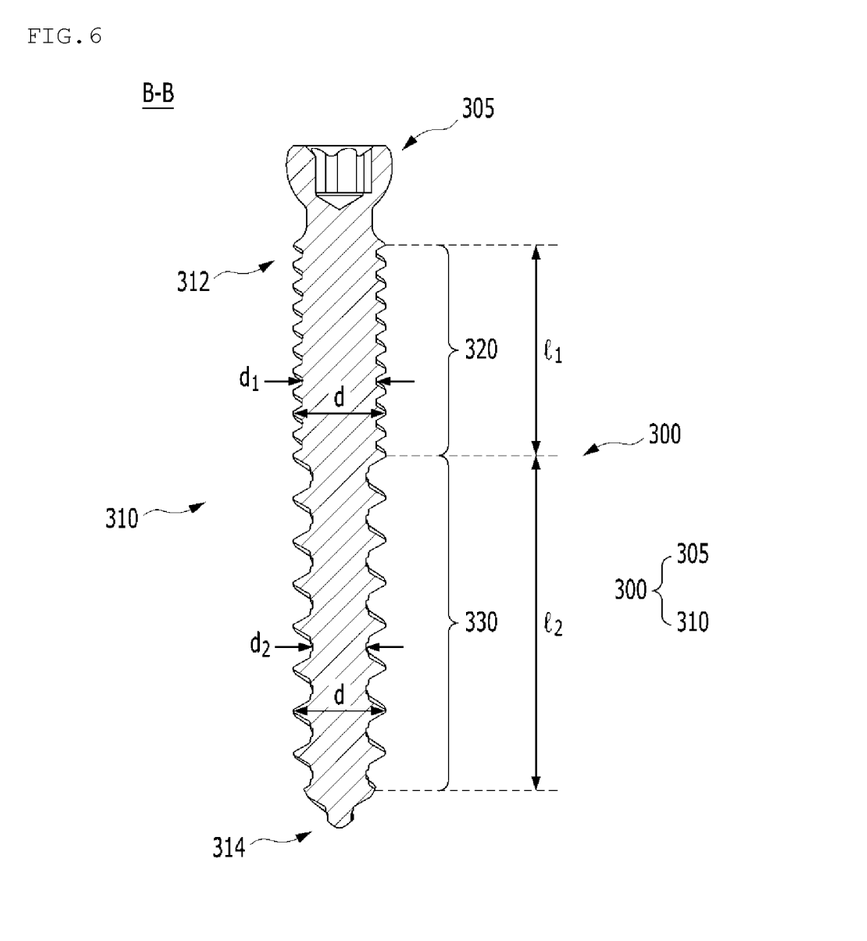
FIG. 6 is a cross-sectional view in direction B-B shown in FIG. 3.

Referring to FIG. 6, a minor diameter $d_1$ of the first screw part 320 is larger than a minor diameter $d_2$ of the second screw part 330 and is formed with a fixed size throughout the same. Since the first screw part 320 is embedded in the cortical bone 102 comprising compact and rigid tissue, it has a larger minor diameter than the second screw part 330. The minor diameter $d_2$ of the second screw part 330 entirely has a fixed size except for the distal end 314. Further, the second screw part 330 is formed with a relatively small minor diameter $d_2$ such that it could be properly coupled to the soft and tender cancellous bone 100.

A major diameter 'd' of the first screw part 320 is equal to that of the second screw part 330. However, the minor diameters of both of these screw parts have a relationship of $d_1 > d_2$, preferably $d_1 = (1.3 \sim 1.4) * d_2$. Since the first screw part 320 is embedded in the compact and rigid cortical bone 102, it does not matter if the screw thread has a shallow depth. However, the second screw part 330 is embedded in the loose and soft cancellous bone 100 and, in order to widen an area contacting cancellous tissue, it is preferable to have a desired distance between the relief screw threads and further ensure a relatively large depth between the relief screw threads.

Hereinafter, the intaglio screw threads will be more concretely described.

The intaglio screw threads 322 and 324 in the second screw part 330 are formed by cutting the middle portion of a threaded root between the relief screw threads 321 and 323 with a predetermined width and a predetermined depth.

Referring to FIGS. 3 and 4, the predetermined width of the intaglio screw threads 322 and 324 corresponds to a bottom width of the relief screw threads 321 and 323. More particularly, the predetermined width of the intaglio screw threads 322 and 324 is substantially equal to a width of a portion of the second screw part 330, which contacts the relief screw threads 321 and 323. This is because the relief screw threads 322 and 324 in the first screw part 320 are changed into the intaglio screw threads 322 and 324 in the second screw part 330.

The intaglio screw threads 322 and 324 in the second screw part 330 are formed by cutting a corresponding portion, at which a height of the relief screw threads 322 and 324 is finally eliminated after being gradually decreased from an end point of the relief screw threads 322 and 324 in the first screw part 320 along a circumference of the screw body 310, with a predetermined depth. More particularly, the intaglio screw threads are formed by cutting a corresponding portion, at which the relief screw threads are not formed, to achieve a width corresponding to the bottom width of the relief screw threads 322 and 324 as well as the predetermined depth.

Referring to the enlarged views in FIGS. 3 and 4, it can be seen that a height of the relief thread 324 at the end point of the first screw part 320 is gradually decreased along the circumference of the screw body 310 and is inclined to form a slope s. Further, a height of the relief thread 322 is also gradually decreased along the circumference of the screw body 310, although such variation (slope, s) occurs at the rear side of the screw body 310 and is not shown in the figures.

Briefly, the intaglio screw threads are formed by cutting a corresponding portion, at which the height of the relief screw threads 322 and 324 is finally eliminated after being gradually decreased from the end point of the first screw part 320, to achieve a width as well as the predetermined depth corresponding to the bottom width of the relief screw threads 322 and 324. That is, cutting the original site of the relief threads 322 and 324, at which these had existed, until reaching a predetermined depth, may form the intaglio screw threads.

The intaglio screw threads 322 and 324 obtained according to the process described above will be formed to have a width of 1 to 1.5 mm and a depth of 0.3 to 0.5 mm. Formation of the intaglio screw threads 322 and 324 having such width and depth as defined above in the second screw part 330 may allow the second screw part 330 to have a greater contact area with the cancellous bone 100 tissues to thus enable stronger coupling thereto, compared to existing pedicle screws.

As described above, it would be understood that a fundamental technical spirit of the present invention is to provide a pedicle screw with quadruple screw threads, having advantages in that: the quadruple screw threads are provided in the whole pedicle screw, so as to move forward at 4-fold higher speed than a single screw thread when a screw is inserted and fixed to a pedicle; and intaglio screw threads are formed at a position to which the cancellous bone is fixed, so that the cancellous bone tissue may penetrate between the intaglio screw threads, thereby accomplishing further stronger coupling force not only to the cortical bone but also to the cancellous bone.

In addition, it would of course be understood that a variety of different modifications and applications may be possible by a person having ordinary skill in the art, without departing from the fundamental technical spirit and scope of the present invention.

DESCRIPTION OF SYMBOLS

100 . . . Cancellous bone
101 102 . . . Cortical bone
300 . . . Pedicle screw
301 305 . . . Joint head
310 . . . Screw body
311 312 . . . Proximal end
314 . . . Distal end
315 320 . . . First screw part
321, 322, 323, 324 . . . Screw thread
330 . . . Second screw part
331 s . . . slope
d . . . Major diameter
$d_1$ . . . Minor diameter of first screw part
$d_2$ . . . Minor diameter of second screw part

The invention claimed is:

1. A pedicle screw with quadruple screw threads, comprising:
a screw body extending from a proximal end to a distal end, so as to be fixed to a vertebra;
a joint head provided at an end of the screw body;
a first screw part, which is formed from the proximal end of the screw body and has a quadruple screw thread pattern for fixing the same to a cortical bone; and
a second screw part, which is formed following the first screw part toward the distal end and has another quadruple screw thread pattern for fixing the same to a cancellous bone,
wherein the quadruple screw pattern formed in the first screw part is a relief pattern throughout the same, while two lines of screw threads in the second screw part are formed in relief but another two lines of screw threads in the same are formed in intaglio,
wherein among the screw threads formed in the second screw part, the screw thread having relief and the screw thread having intaglio are formed by turns.

2. The pedicle screw according to claim 1, wherein each of the screw threads forming the quadruple screw thread pattern in the first screw part is formed at a position 90° from a circumference of the screw body.

3. The pedicle screw according to claim 1, wherein the second screw part occupies ½ to ⅔ of the screw body.

4. The pedicle screw according to claim 1, wherein a minor diameter of the first screw part is larger than that of the second screw part and is formed with a fixed size throughout the same, and a minor diameter of the second screw part entirely has a fixed size except for the distal end.

5. The pedicle screw according to claim 1, wherein the intaglio screw thread in the second screw part is formed by cutting the center portion of a threaded root between the relief screw threads with a predetermined width and a predetermined depth.

6. The pedicle screw according to claim 5, wherein the predetermined width of the intaglio screw thread corresponds to a bottom width of the relief screw thread.

7. The pedicle screw according to claim 1, wherein the intaglio screw thread in the second screw part is formed by cutting a corresponding portion, at which a height of the relief screw thread is finally eliminated after being gradually decreased from an end point of the relief screw thread in the first screw part along a circumference of the screw body, with a predetermined depth.

8. The pedicle screw according to claim 7, wherein the intaglio screw thread is formed by cutting a corresponding portion, at which the relief screw thread is not formed, to achieve a width corresponding to a bottom width of the relief screw thread as well as the predetermined depth.

* * * * *